(12) United States Patent
Vettraino et al.

(10) Patent No.: US 8,276,436 B2
(45) Date of Patent: Oct. 2, 2012

(54) VACUUM ASSISTED NUT DROP TEST

(75) Inventors: Marino Vettraino, Lake Orion, MI (US); David Lee Hicks, Fowlerville, MI (US)

(73) Assignee: Toyota Motor Engineering & Manufacturing North America, Inc., Erlanger, KY (US)

( * ) Notice: Subject to any disclaimer, the term of this patent is extended or adjusted under 35 U.S.C. 154(b) by 228 days.

(21) Appl. No.: 12/690,155

(22) Filed: Jan. 20, 2010

(65) Prior Publication Data

US 2011/0174090 A1 Jul. 21, 2011

(51) Int. Cl.
*B23Q 17/09* (2006.01)
*G01N 3/00* (2006.01)

(52) U.S. Cl. ............ 73/104; 73/866; 73/7; 73/12.06

(58) Field of Classification Search .......... None
See application file for complete search history.

(56) References Cited

U.S. PATENT DOCUMENTS

| | | | |
|---|---|---|---|
| 2,414,653 A * | 1/1947 | Lookholder | 335/285 |
| 3,404,556 A * | 10/1968 | Kameras | 73/7 |
| 3,985,026 A | 10/1976 | Griffin et al. | |
| 4,065,964 A | 1/1978 | Cunningham | |
| 4,791,807 A | 12/1988 | Oechsle | |

FOREIGN PATENT DOCUMENTS

KR 569373 B1 * 4/2006

OTHER PUBLICATIONS

Derwent Summary. Patent KR569373B1.*

* cited by examiner

*Primary Examiner* — Hezron E Williams
*Assistant Examiner* — Mark A Shabman
(74) *Attorney, Agent, or Firm* — Gifford, Krass, Sprinkle, Anderson & Citkowski, P.C.

(57) ABSTRACT

The present invention provides for an apparatus for testing a surface coating. An elongated tube having a first end and a second end is provided wherein said second end is open to a holding container. The first end of the elongated tube farther includes a funnel. A planar test panel is adapted to hold a variety of materials to be tested. Such materials include paint, coatings, tape, or other like materials. A separator is fluidly connected to the holding container via a first conduit. A vacuum is fluidly connected to a separator by means of a second conduit. A tester places a plurality of loose test pieces, such as metal nuts or small rocks, into the funnel and the loose test pieces fall through the elongated tube and onto the planar test panel. The loose test pieces then fall into the holding container. The vacuum creates suction through said separator and through the conduits into the holding container thereby removing the loose test pieces from the holding container through the conduit and into the separator. The loose test pieces can then be removed from the separator, and the testing process may easily be repeated.

17 Claims, 2 Drawing Sheets

VACUUM ASSISTED NUT DROP TEST

FIELD OF THE INVENTION

This invention relates to coating testing equipment, in particular an apparatus for coating testing with improved test repetition capabilities.

BACKGROUND OF THE INVENTION

Paints, coatings, and tapes are commonly tested by dropping loose test pieces, such as pebbles or metal nuts, onto a test panel holding the sample to be tested. Such an apparatus typically comprises a funnel and elongated tube disposed above a test panel. The test panel is adapted to hold the paint, coating, or tape to be tested. Loose test pieces are placed in the funnel and drop through the elongated tube onto the test panel. This method is designed to test chipping resistance qualities of the point, coating, or tape. The loose test pieces are measured in terms of mass, and the total mass of the loose test pieces needed to cause the test panel to fail is measured. Once the loose test pieces hit the test panel, they fall into a holding container. The test is repeated by removing the loose test pieces from the container and repouring them into the funnel. This procedure is repeated until the test panel reaches failure or until otherwise indicated. Removing the loose test pieces from the holding container becomes a monotonous and time-consuming task for the tester. Accordingly, there is a need for an improved method of removing test pieces from a holding container after the test is complete.

SUMMARY OF THE INVENTION

The present invention provides for an apparatus for testing a surface coating. An elongated tube having a first end and a second end wherein said second end is open to a holding container. The first end of the elongated tube further includes a funnel. A planar test panel is adapted to hold a variety of materials to be tested. Such materials include paint, coatings, tape, or other like materials. A separator is fluidly connected to the holding container via a first conduit. A vacuum is fluidly connected to a separator by means of a second conduit. A tester places a plurality of loose test pieces, such as metal nuts or small rocks, into the funnel and the loose test pieces fall through the elongated tube and onto the planar test panel. The loose test pieces then fall into the holding container. The vacuum creates suction through said separator and through said conduits into the holding container thereby removing the loose test pieces through the conduit and into the separator. The loose test pieces can then be removed from the separator, and the test process may easily be repeated.

BRIEF DESCRIPTION OF THE DRAWINGS

FIG. 3 is a perspective view of the holding container and connecting conduit.

DETAILED DESCRIPTION OF THE PREFERRED EMBODIMENTS

The present invention provides for a method and apparatus for testing a plurality of materials. The apparatus and method generally test chipping and chipping resistance of paints, coatings, tapes, and other like materials. The apparatus and method provide for an improvement to this testing process whereby repetition of the method is made easier. The invention provides for a vacuum and separator connected by a plurality of conduits connected to a holding container. The vacuum creates suction through said separator and through said conduits into the holding container thereby removing the loose test pieces through the conduit and into the separator. The loose test pieces can then be removed from the separator, and the testing process may easily be repeated.

Figure 1:
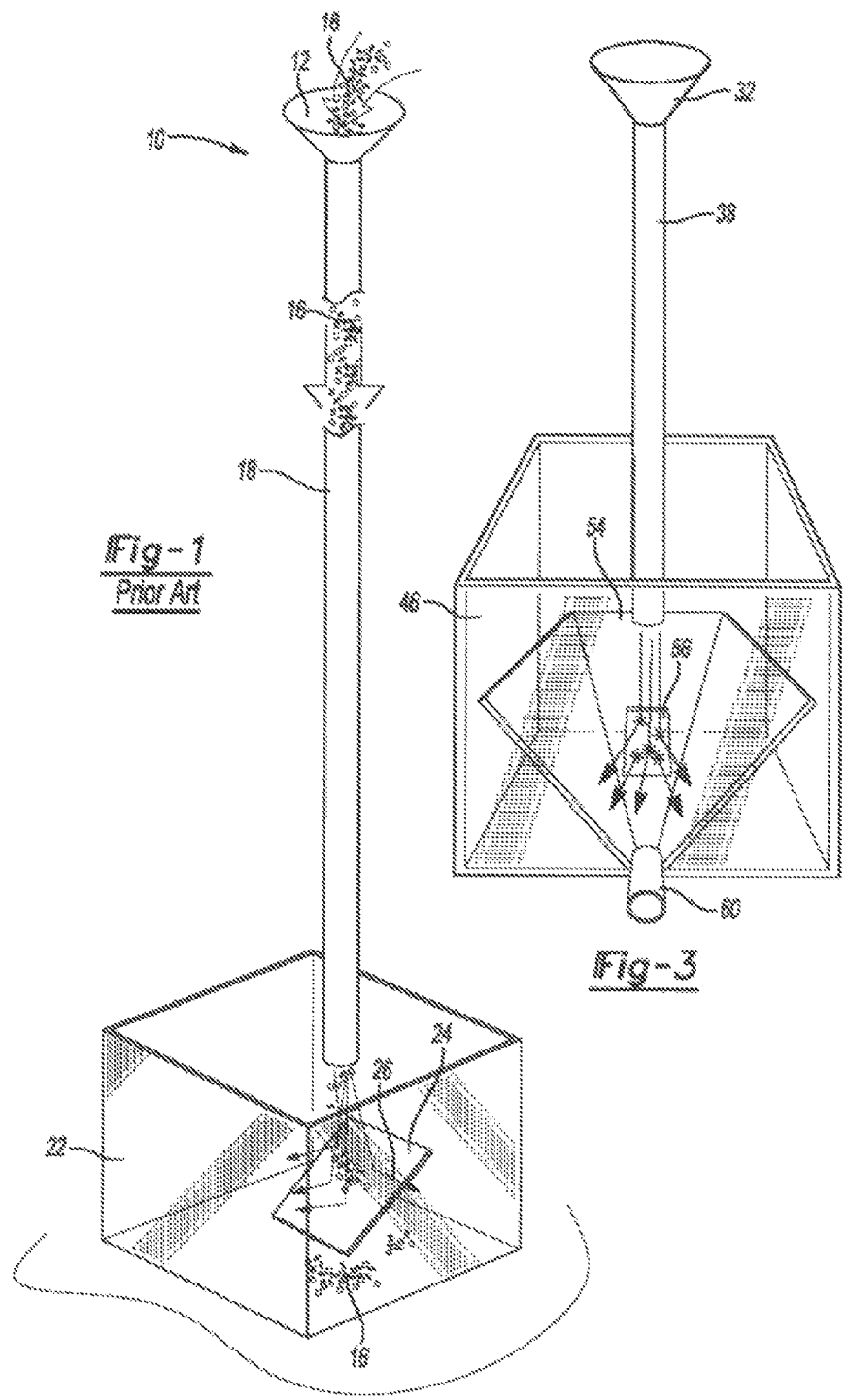
FIG. 1 is a perspective view of the prior art.

The prior art includes a testing apparatus 10 having a funnel 12 and an elongated tube 18, as shown by FIG. 1. The testing apparatus 10 further includes a holding container 22 having a test panel 24 disposed therein. Loose test pieces 16 are placed into the funnel 12 and subsequently fall through the elongated tube 18 onto the test panel 24 and into the holding container 22. The loose test pieces 16 fall onto the test panel 24 and into the holding container 22 as shown by illustrative arrows 26. The test process is repeated by manually collecting loose test pieces 16 and replacing them into the funnel 12. Repetition of this process is monotonous and time consuming for the tester.

Figure 2:
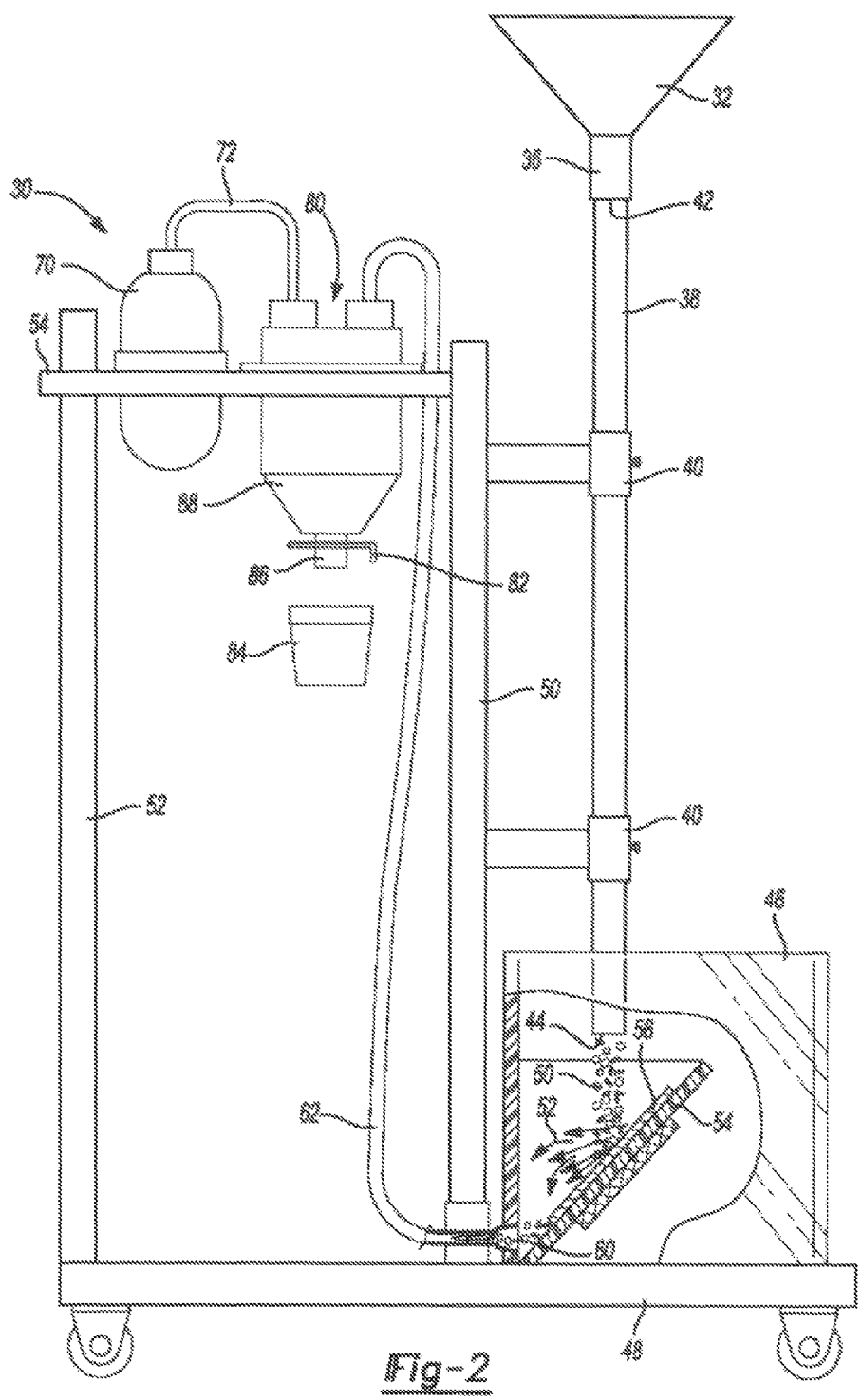
FIG. 2 is a side view of the present invention.

The testing apparatus 30 is an improvement on the prior art, enabling the tester to more efficiently repeat the testing process. An elongated tube 38, having a first end 42 and a second end 44, is mounted generally vertical, as shown by FIGS. 2 and 3. The first end 42 includes a funnel 32 connected to the elongated tube 38 by means of a connector 36. The connector 36 may be tape, adhesive or other connection member. The second end 44 of the elongated tube 38 is open to the holding container 46. Loose test pieces 50 are placed into the funnel 32, drop through the elongated tube 38, and out of the second end 44 onto a test panel 56. The test panel 56 is covered with a coating, paint, tape, or other material to be tested. The test panel 56 is tested until failure or until a specified test standard is met. Testing is measured in terms of the mass of loose test pieces 50.

The test panel 56 is mounted or otherwise adhered to panel 54. The test panel 56 may be glued, clipped, or otherwise attached to the panel 54. In an alternative embodiment, the panel 54 includes a magnet allowing a ferrous test panel 56 to securely attach to the panel 54 during testing. Arrows 52 indicate the path of loose test pieces 50 as they exit the second end 44 of the elongated tube 38 and as the loose test pieces 50 hit the test panel 56 and fall into the holding container 46.

A separator assembly 80 is provided having a body 88, a collection cup 84, and a release valve 82. The separator assembly 80 is fluidly connected to the holding container 46 by a conduit 62. The conduit 62 may be a flexible plastic tubing or metal tubing. The conduit 62 is connected to the holding container 46 by means of a connector 60. The collection cup collects the loose test pieces 50. The collection cup 84 is easily removed from the separator assembly 80. Once the test is complete, a tester may remove the collection cup 84 and repeat the test.

A vacuum 70 is also provided having a connection 74. The vacuum 70 is connected to the separator apparatus 80 by means of a conduit 72. The conduit 72 may be plastic tubing or metal tubing. The vacuum 70, the separator apparatus 80, conduit 72, conduit 62, and the holding container 46 are each fluidly connected to one another. The vacuum 70 creates suction through the separator apparatus 80 and into the holding container 46 thereby removing loose test pieces 50 through the conduit 62 and into the separator apparatus 80. The separator apparatus 80 separates the loose test pieces 50 and collects the loose test pieces 50 into the collection cup 84 through the valve 86. Once all loose test pieces 50 have been collected into the collection cup 84 of the separator apparatus 80, the release valve 82 enables removal of the collection cup 84 from the separator apparatus. The collection cup 84 containing loose test pieces 50 is removed. Once removed, loose test pieces 50 in the collection cup 84 may be replaced into the funnel 32 of the testing apparatus 30 to repeat the process.

The testing apparatus 30 is placed on a cart 48. The cart 48 may further include support members 50, 52 and 54 to hold necessary components such as the vacuum 70, the separator apparatus 80, and the holding container 46. The elongated tube 38 is further supported by connection members 40 which connect the elongated tube 38 to support member 50. Support member 54 is essentially a table holding the vacuum 70 in the separator apparatus 80.

The invention has been described in an illustrative manner. It is therefore to be understood that the terminology used is intended to be in the nature of words of description rather than of limitation. Many modifications and variations of the invention are possible in light of the above teachings. Thus, within the scope of the appended claims, the invention may be practiced other than as specifically described.

It is claimed:

1. A test apparatus for testing coatings using a plurality of loose test pieces, the apparatus comprising:
   a frame;
   an elongated tube mounted to the frame, the elongated tube having a first end and second end;
   a holding container mounted to the frame and disposed below the elongated tube, said holding container having a planar test panel;
   the elongated tube adapted to accept the plurality of loose test pieces, the elongated tube adapted to have the plurality of loose test pieces enter the first end of the elongated tube and exit through the second end of the elongated tube and fall onto the planar test panel and into the holding container; and
   a separator mounted to the frame, a vacuum mounted to the frame and fluidly connected to the separator, a conduit fluidly connecting the holding container to the separator to draw the plurality of loose test pieces from the holding container through the tube into the separator.

2. The apparatus of claim 1, wherein the first end of the elongated tube further includes a funnel.

3. The apparatus of claim 1, wherein the planar test panel is mounted to the holding container at a predetermined angle.

4. The apparatus of claim 3, wherein the predetermined angle ranges between 10° and 80° relative to a horizontal plane.

5. The apparatus of claim 1, wherein the planar test panel is mounted to a planar mounting panel.

6. The apparatus of claim 5, wherein the test panel is a ferrous material.

7. The apparatus of claim 6, wherein the planar mounting panel is magnetized to hold the ferrous test panel to the planar mounting panel.

8. The apparatus of claim 1, wherein the test panel is adapted to hold a paint coating sample.

9. The apparatus of claim 1, wherein said test panel is adapted to hold a tape sample.

10. The apparatus of claim 1, wherein the plurality of loose test pieces are brass nuts.

11. The apparatus of claim 1, wherein the plurality of loose test pieces are pebbles.

12. The apparatus of claim 1, wherein the separator further includes a gate valve.

13. The apparatus of claim 12, wherein the gate valve includes a holding cup adapted to hold the plurality of loose test pieces.

14. The apparatus of claim 13, wherein the gate valve opens to the holding cup and the holding cup collects the plurality of loose test pieces.

15. A method for performing a test for testing a coating, said method including the steps of:
   placing a plurality of loose test pieces into a funnel, the funnel connected to a first end of an elongated tube, the plurality of loose test pieces falling through the elongated tube onto a test panel, the plurality of loose test pieces collecting in a holding container;
   vacuuming the plurality of loose test pieces from the holding container into a separator, the separator collecting the plurality of loose test pieces in a collection cup;
   removing the collection cup from the separator; and
   repeating the steps of placing the plurality of loose test pieces into the funnel, vacuuming the plurality of loose test pieces into the separator, and removing the plurality of loose test pieces from the separator until a testing process is complete.

16. The method of claim 15, wherein the method for performing a test for testing a coating is repeated until the coating fails.

17. The method of claim 15, wherein the test for testing a coating is repeated until a predetermined mass of the plurality of loose test pieces has been dropped onto the test panel.

* * * * *

UNITED STATES PATENT AND TRADEMARK OFFICE
CERTIFICATE OF CORRECTION

PATENT NO. : 8,276,436 B2  
APPLICATION NO. : 12/690155  
DATED : October 2, 2012  
INVENTOR(S) : Marino Vettraino et al.

Page 1 of 1

It is certified that error appears in the above-identified patent and that said Letters Patent is hereby corrected as shown below:

In the Specification

At column 1, line number 19, Delete "point", Insert --paint--.

Signed and Sealed this  
Ninth Day of December, 2014

Michelle K. Lee  
*Deputy Director of the United States Patent and Trademark Office*